US00PP36114P2

(12) United States Plant Patent
Grazzini

(10) Patent No.: US PP36,114 P2
(45) Date of Patent: Sep. 17, 2024

(54) ***DIERVILLA* PLANT NAMED 'G2X88544VAR'**

(50) Latin Name: ***Diervilla* x *splendens***
Varietal Denomination: G2X88544VAR

(71) Applicant: GardenGenetics LLC, Columbus, OH (US)

(72) Inventor: Richard A. Grazzini, Columbus, OH (US)

(73) Assignee: Garden Genetics LLC, Columbus, OH (US)

( * ) Notice: Subject to any disclaimer, the term of this patent is extended or adjusted under 35 U.S.C. 154(b) by 0 days.

(21) Appl. No.: 18/541,503

(22) Filed: Dec. 15, 2023

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Diervilla* plant named 'G2X88544VAR' is disclosed, characterized by a rounded, compact habit, and variegated dark green and cream leaves with a reddish-pink flush. The new variety is a *Diervilla*, normally produced as an outdoor garden or container plant.

3 Drawing Sheets

Latin name of the genus and species: *Diervilla* x *splendens*.
Variety denomination: 'G2X88544VAR'.

BACKGROUND OF THE INVENTION

The new *Diervilla* cultivar is a product of a naturally-occurring whole plant mutation of *Diervilla* x *splendens* 'G2X88544', U.S. Plant Pat. No. 27,548. The new variety was identified as a potentially interesting selection in 2017 at a nursery in Grand Haven, Michigan.

Asexual reproduction of the new cultivar 'G2X88544VAR' by softwood cuttings was first performed during 2017 at research greenhouse in Grand Haven, Michigan. Subsequent propagation has shown that the unique features of this cultivar are stable and reproduced true to type in several successive generations.

SUMMARY OF THE INVENTION

The cultivar 'G2X88544VAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G2X88544VAR'. These characteristics in combination distinguish 'G2X88544VAR' as a new and distinct *Diervilla* cultivar:

1. Stable, consistent, cream-colored marginal variegation on dark green leaves.
2. Reddish-pink flush that fades to a lighter blush as leaves develop.
3. Rounded/compact habit.

PARENT COMPARISON

Plants of the new cultivar 'G2X88544VAR' are similar to plants of the parent variety, in most horticultural characteristics, however, plants of the new cultivar 'G2X88544VAR' differ in the following:

1. Foliage of the new variety is variegated, while the foliage of the parent is non-variegated.
2. New growth of the new variety is reddish-pink, while the new growth of the parent is reddish-orange.

COMMERCIAL COMPARISON

Plants of the new cultivar 'G2X88544VAR' can also be compared to the commercial variety *Diervilla* 'LPDC PODARAS', U.S. Plant Pat. No. 19,391. The varieties are similar in most horticultural characteristics, however 'G2X88544VAR' differs in the following:

1. New growth of the new variety is reddish-pink, while the new growth of this comparator is green.
2. Plants of this comparator have a suckering tendency, while plants of the new variety do not.

BRIEF DESCRIPTION OF THE PHOTOGRAPHS

The accompanying photograph in FIG. 1 illustrates in full color a typical plant of 'G2X88544VAR', grown in a 2 gallon container.

Figure 1:
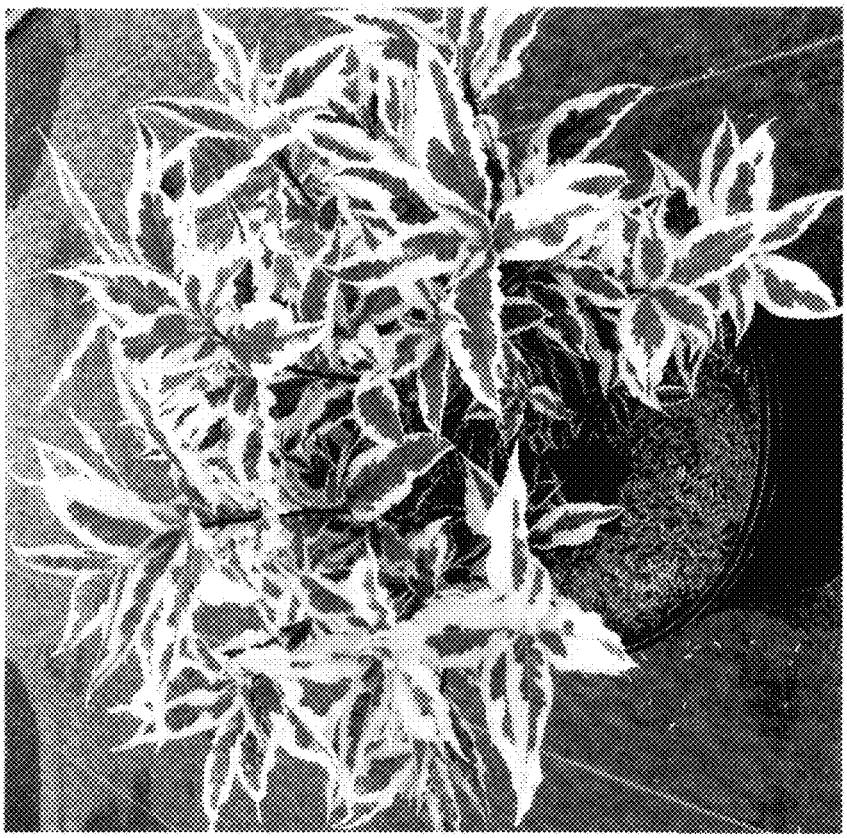
Figure 2:
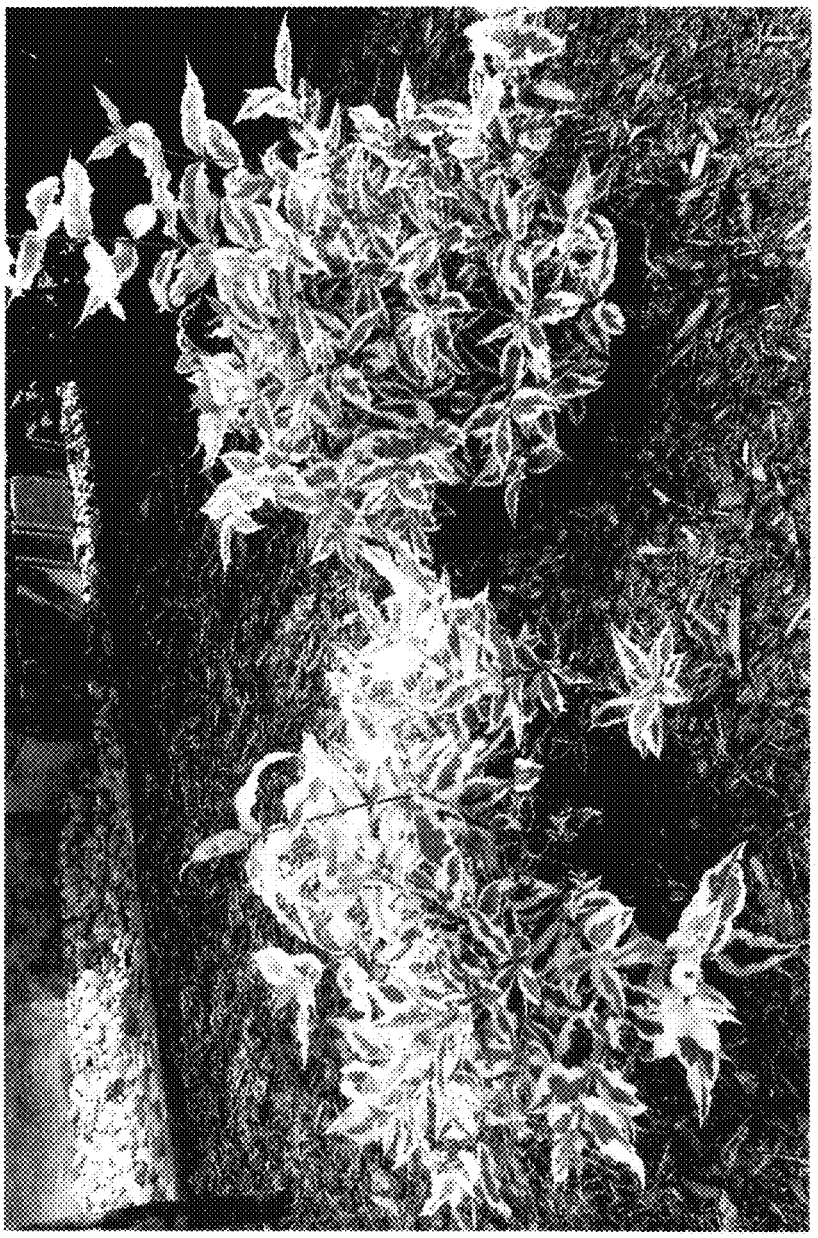
FIG. 2 illustrates in full color typical plants of 'G2X88544VAR', grown in a field in Grand Haven, Michigan. Plants are about 2 years old.
Figure 3:
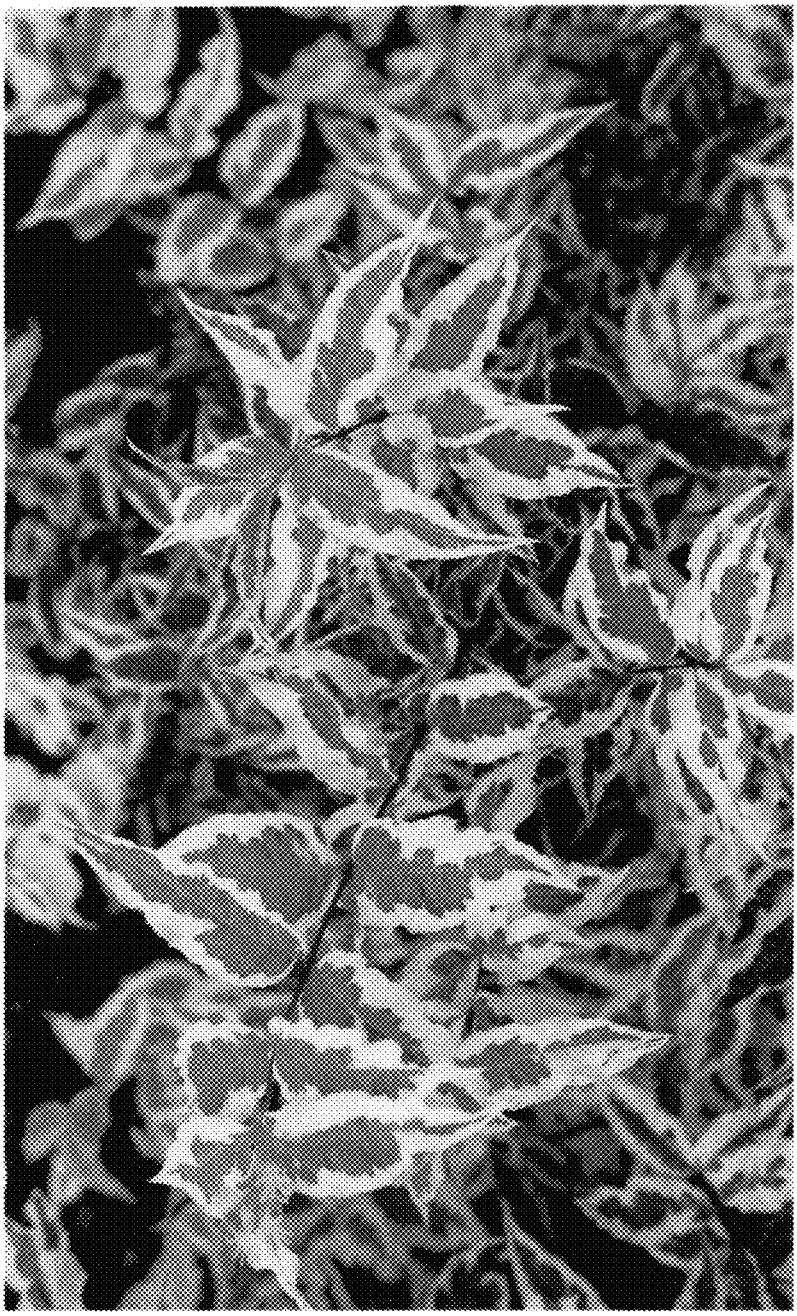
FIG. 3 is a close-up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'G2X88544VAR' plants grown in a poly house in Grand Haven, Michigan. Measurements were taken during August of 2023. The plants were approximately 2 years old. The growing temperature ranged from 18° C. to 27° C.

during the day, and 5° to 10° C. at night. Measurements and numerical values represent averages of typical plant types.

Botanical classification: *Diervilla* x *splendens* 'G2X88544VAR'.

PROPAGATION

Time to initiate roots: About 10 to 21 days at approximately 18° to 27° C.

Time to produce a rooted young plant: About 21 days in summer at approximately 18° to 27° C.

Root description: Medium to thick, intermediate texture, moderately dense and moderately freely branching. Roots white to tan, not accurately measured with R.H.S. chart.

PLANT

Plant type: Perennial shrub.
Age of plant described: Approximately 3 years old.
Pot size of plant described: Field grown.
Growth habit: Upward and outwards.
Overall plant shape: Rounded, upright, compact.
Height: 85 cm.
Plant spread: 95 cm.
Growth rate: Moderate to rapid.
Plant vigor: Quite vigorous.
Branching characteristics: Basal, some pinching required to encourage round habit.
Length of primary lateral branches: 50 to 70 cm.
Diameter of lateral branches: 3 to 5 mm.
Quantity of lateral branches: 20 to 30.
Stem:
- *Shape*.—Rounded with ridges set 180° apart.
- *Aspect*.—40° to 80°.
- *Strength*.—Strong, fairly rigid.
- *Pubescence*.—None.
- *Color*.—New Growth: Upper side: RHS Greyed-Red 182A. Under side: Near RHS Yellow-Green 145C. Old Growth (bark): RHS Grey-Brown 199A to 199B.

Internode length: 6 cm.

FOLIAGE

Leaf:
- *Arrangement*.—Opposite, before and after flowering.
- *Length*.—10 cm.
- *Width*.—3 cm.
- *Shape of blade*.—Narrowly elliptic to lanceolate.
- *Apex*.—Acuminate.
- *Base*.—Attenuate.
- *Margin*.—Serrate, margin has an undulating quality.
- *Texture of top surface*.—Glabrous; leaf surface has a ruffled or rippled quality.
- *Texture of bottom surface*.—Glabrous; leaf surface has a ruffled or rippled quality; pronounced midrib.
- *Color*.—Young foliage upper side: Marginal variegation: Near RHS Greyed-Red 180D. Base color: RHS Yellow-Green 147B tinted Greyed-Red 180D. Young foliage under side: Marginal variegation: RHS Greyed-Red 180D. Base color: RHS Yellow-Green 147B tinted Greyed-Red 180D. Mature foliage upper side: RHS Green NN137C with Greyed-Yellow 160C marginal variegation. Mature foliage under side: RHS Yellow-Green 147B with Greyed-Yellow 160C marginal variegation.
- *Venation*.—Type: Pinnate. Color, upper side: RHS Yellow-Green 145C. Color, under side: RHS Yellow-Green 145C.
- *Petiole*.—Length: 3 mm. Diameter: 2 mm. Color, upper side: RHS Greyed-Red 182A. Color, lower side: Near RHS Yellow-Green 145C. Texture: Glabrous.

FLOWER

Natural flowering season: July to August.
Inflorescence type and habit: Simple cyme.
Quantity of flowers per inflorescence: 3.
Quantity of flowers per lateral stem: About 10.
Quantity of buds per lateral stem: About 5.
Quantity of flowers and buds per plant: 300 to 400.
Inflorescence size:
- *Diameter*.—2.5 cm.
- *Height*.—3 cm.

Individual flowers:
- *Form*.—Salverform.
- *Habit*.—Single flowers clustered at the terminal ends of lateral branches in groups of 3.
- *Aspect*.—Outward.
- *Size*.—Diameter: 1 cm. Depth: 1.5 cm. Flower Throat Diameter: 3 mm. Flower Tube Diameter: 2 mm. Flower Tube Length: 5 mm.
- *Persistence*.—Self-cleaning.
- *Fragrance*.—None.

Petal:
- *Arrangement*.—Stellate; single whorl of narrow petals.
- *Number*.—5 per flower.
- *Shape*.—Linear.
- *Tip*.—Fused.
- *Margin*.—Entire.
- *Length*.—6 mm from throat.
- *Width*.—2 mm.
- *Texture*.—Upper: Glabrous, soft, and silky. Lower: Glabrous, soft, and silky. Tube texture: Glabrous. Throat texture: Glabrous.
- *Color*.—When opening: Upper surface: RHS Yellow 4B. Lower surface: RHS Yellow 4B. Fully opened: Upper surface: RHS Yellow 4B. Lower surface: RHS Yellow 4B. Flower tube color: RHS Yellow 4B. Flower throat color: RHS Yellow 4B.

Petaloids: None present.
Bud:
- *Shape*.—Oblong/spatulate.
- *Length*.—1 cm.
- *Diameter*.—2 mm.
- *Color*.—RHS Yellow-Green 150C.

Sepals:
- *Appearance*.—Needle-like; diminutive & inconspicuous.
- *Shape*.—Acicular.
- *Arrangement*.—Whorl.
- *Length*.—2 mm.
- *Width*.—Less than 1 mm.
- *Margin*.—Entire.
- *Base*.—Fused.
- *Tip*.—Acuminate.
- *Number*.—5.
- *Color*.—RHS Green-White 157C.
- *Texture, upper side*.—Glabrous.
- *Texture, under side*.—Glabrous.
- *Calyx shape*.—Collar-like.

Peduncle:
*Length.*—6 mm.
*Diameter.*—2 mm.
*Color.*—RHS Yellow-Green 145A.
*Orientation.*—90° relative to stem.
*Strength.*—Good.
*Texture.*—Glabrous.
Pedicel:
*Length.*—2 mm.
*Diameter.*—1 mm.
*Angle.*—45° relative to peduncle.
*Strength.*—Good.
*Texture.*—Glabrous.
*Color.*—RHS Yellow-Green 145A.

REPRODUCTIVE ORGANS

Stamens:
*Number.*—5.
*Filament length.*—5 mm.
*Filament color.*—RHS Yellow 4B.
Anthers:
*Shape.*—Linear.
*Length.*—2 mm.
*Color.*—RHS Greyed-Yellow 161A.
*Pollen.*—Moderate.
*Pollen color.*—RHS Yellow-White N144B.
Pistil:
*Number.*—1.
*Length.*—1.5 cm.
*Style.*—Length: 1.4 cm. Color: RHS Yellow-Green 145C.
*Stigma.*—Shape: Globular. Color: RHS Yellow-Green N144B.

OTHER CHARACTERISTICS

Fruits and seeds: Not observed.
Disease/pest resistance: Neither resistance nor tolerance to typical diseases and pests of *Diervilla* have been observed.
Temperature tolerance: The new variety tolerates temperatures from −31° to 38° C.

What is claimed is:

1. A new and distinct cultivar of *Diervilla* plant named 'G2X88544VAR' as herein illustrated and described.

* * * * *